United States Patent
Joung et al.

(10) Patent No.: US 10,160,775 B2
(45) Date of Patent: Dec. 25, 2018

(54) GROUP 4 TRANSITION METAL COMPOUND AND USE THEREOF

(71) Applicant: HANWHA CHEMICAL CORPORATION, Seoul (KR)

(72) Inventors: Ui Gab Joung, Daejeon (KR); Dong Ok Kim, Seoul (KR); Dong Wook Kim, Daejeon (KR); Ah Reum Kim, Gyeonggi-do (KR); Hye Ran Park, Gyeongsangbuk-do (KR); Kil Sagong, Daejeon (KR); Sung Hae Jun, Gyeonggi-do (KR); Chun Sun Lee, Gyeonggi-do (KR); Eun Yeong Hwang, Gyeonggi-do (KR)

(73) Assignee: HANWHA CHEMICAL CORPORATION, Seoul (KR)

( * ) Notice: Subject to any disclaimer, the term of this patent is extended or adjusted under 35 U.S.C. 154(b) by 0 days.

(21) Appl. No.: 15/502,721

(22) PCT Filed: Aug. 28, 2015

(86) PCT No.: PCT/KR2015/009063
§ 371 (c)(1),
(2) Date: Feb. 8, 2017

(87) PCT Pub. No.: WO2016/032280
PCT Pub. Date: Mar. 3, 2016

(65) Prior Publication Data
US 2017/0233415 A1   Aug. 17, 2017

(30) Foreign Application Priority Data
Aug. 28, 2014   (KR) .................. 10-2014-0113533

(51) Int. Cl.
*C08F 4/76*   (2006.01)
*C08F 4/64*   (2006.01)
(Continued)

(52) U.S. Cl.
CPC .................. *C07F 7/00* (2013.01); *C08F 4/16* (2013.01); *C08F 210/16* (2013.01); *C08F 4/64044* (2013.01)

(58) Field of Classification Search
CPC ............. C08F 4/60044; C08F 4/64044; C08F 4/62044
See application file for complete search history.

(56) References Cited

U.S. PATENT DOCUMENTS 3,322,773 A * 5/1967 Colwell ............... C07D 471/04
                                                           504/245
6,399,724 B1 * 6/2002 Matsui .................... C08F 10/00
                                                           502/117
(Continued)

FOREIGN PATENT DOCUMENTS

CN      102781981 A      11/2012
EP        3239156 A1     11/2017
(Continued)

OTHER PUBLICATIONS

First Office Action, Chinese Patent Application No. 201580041866. X, dated May 25, 2018.
(Continued)

*Primary Examiner* — Rip A Lee
(74) *Attorney, Agent, or Firm* — Marshall, Gerstein & Borun LLP

(57) ABSTRACT

The present invention relates to a novel group 4 transition metal compound, a method for preparing the compound, a catalyst composition containing the compound, and a method for preparing a polyolefin, comprising a step for forming a polymerization reaction of olefin monomers in the presence of the catalyst composition. The group 4 transition metal compound of the present invention exhibits an excellent catalytic activity and has excellent thermal stability in a polyolefin synthesis reaction, and thus can be used even in (Continued)

a polyolefin synthesis reaction at a high temperature. In addition, the compound of the present invention can be advantageously used in the synthesis process of grade-controlled polyolefin since the weight average molecular weight of the synthesized polyolefin and the octane content in the polymer can be adjusted by varying the kinds of center metal and ligand.

17 Claims, 1 Drawing Sheet

(51) Int. Cl.
*C07F 7/00* (2006.01)
*C08F 4/16* (2006.01)
*C08F 210/16* (2006.01)

(56) References Cited

U.S. PATENT DOCUMENTS

| | | | |
|---|---|---|---|
| 7,973,116 B2 | 7/2011 | Hagadorn et al. | |
| 8,362,162 B2 | 1/2013 | Hustad et al. | |
| 8,372,927 B2 * | 2/2013 | Figueroa | C07F 7/00 526/161 |
| 8,729,201 B2 * | 5/2014 | Fontaine | C07D 251/40 526/160 |
| 8,748,547 B2 * | 6/2014 | Park | C08F 10/00 526/160 |
| 9,062,146 B2 * | 6/2015 | Noh | C08F 297/083 |

FOREIGN PATENT DOCUMENTS

| | | |
|---|---|---|
| EP | 3239157 A1 | 11/2017 |
| KR | 20070072236 A | 7/2007 |
| KR | 20080080526 A | 9/2008 |
| KR | 20110009943 A | 1/2011 |
| KR | 20110031995 A | 3/2011 |
| KR | 20110053335 A | 5/2011 |
| KR | 20130008559 A | 1/2013 |

OTHER PUBLICATIONS

Philip P. Fontaine, et. al., "Hafnium Amidoquinoline Complexes: Highly Active Olefin Polymerization Catalysts with Ultrahigh Molecular Weight Capacity", Organometallics, vol. 31, pp. 6244-6251.
Thomas R. Boussie, et. al., "A Fully Integrated High-Throughput Screening Methodology for the Discovery of New Polyolefin Catalysts: Discovery of a New Class of High Temperature Single-Site Group (IV) Copolymerization Catalysts", JACS, vol. 125, No. 14, pp. 4306-4317.
International Search Report for International Application No. PCT/KR2015/009063, dated Dec. 4, 2015.
Office Action, Korean Patent Application No. 10-2014-0113533, dated Mar. 7, 2018.
Extended European Search Report for EP Application No. 15836333.3, dated Mar. 21, 2018.
Eun Yeong Hwang et al., Preparation of octahydro- and tetrahydro-[1,10]phenanthroline zirconium and hafnium complexes for olefin polymerization. Dalton Transactions, vol. 44, No. 8, Jan. 22, 2015, pp. 3845-3855.
Chun Ji Wu et al., Ortho Lithiation of Tetrahydroquinoline Derivatives and Its Use for the Facile Construction of Polymerization Catalysts. 2007, vol. 26(27), pp. 6685-6687, © 2017 American Chemical Society.
International Preliminary Report on Patentability for International Application No. PCT/KR2015/009063, dated Feb. 28, 2017 (English Translation).
Written Opinion of the International Searching Authority for International Application No. PCT/KR2015/009063 dated Apr. 12, 2015 (English Translation).

* cited by examiner

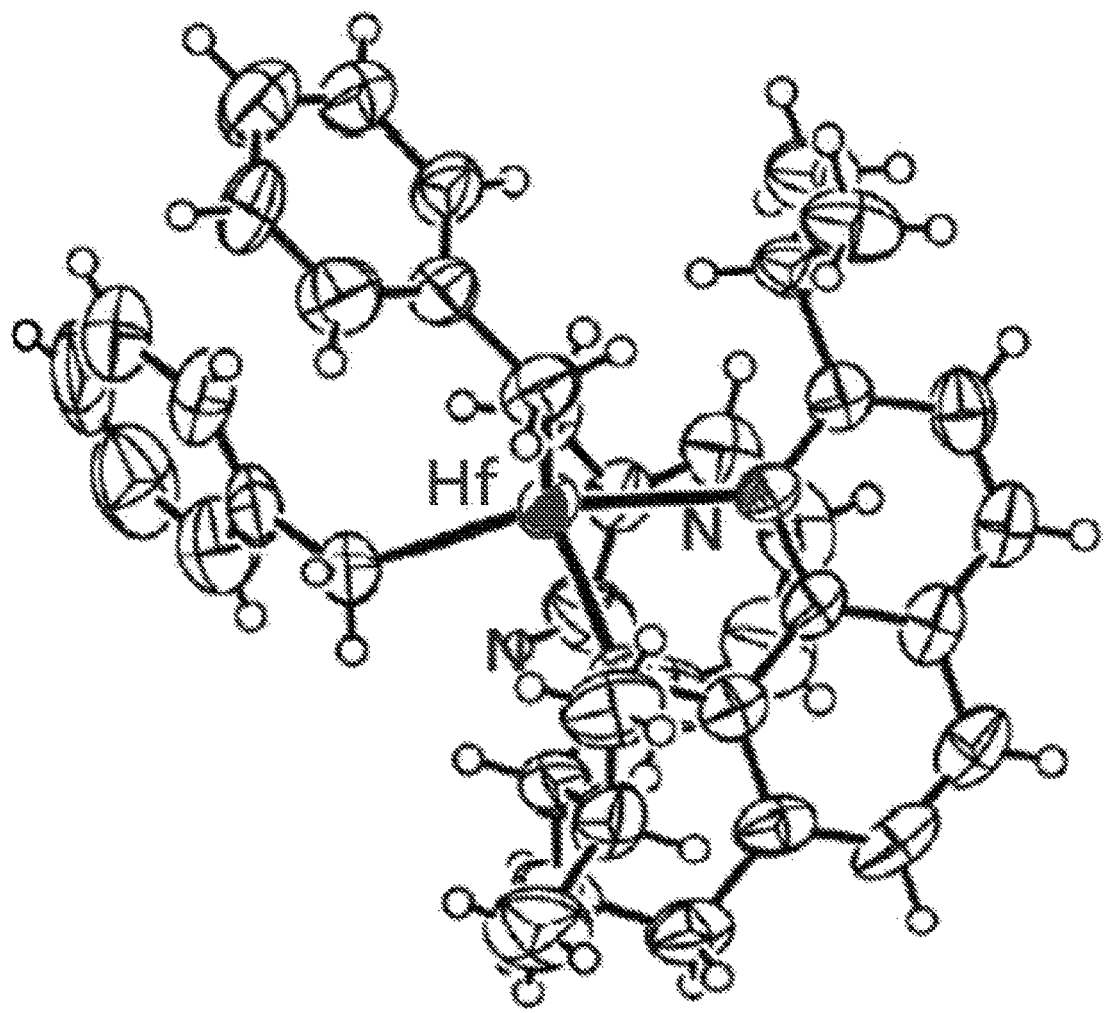

GROUP 4 TRANSITION METAL COMPOUND AND USE THEREOF

CROSS REFERENCE TO RELATED APPLICATIONS

This application is the U.S. National Phase of International Patent Application No. PCT/KR2015/009063 filed Aug. 28, 2015, which claims the benefit of Korean Patent Application No. 10-2014-0113533 filed Aug. 28, 2014, the respective disclosures of which are each incorporated herein by reference in their entireties.

BACKGROUND

Technical Field

The present invention relates to a novel Group 4 transition metal compound, a preparation method thereof, a catalyst composition comprising the same, and a polyolefin preparation method comprising a step of carrying out polymerization of an olefin monomer in the presence of the catalyst composition.

Background Art

A polyolefin is used in real life for a material of various objects, such as shopping bags, vinyl greenhouses, fishing nets, cigarette wrappers, ramen noodle packs, yogurt containers, battery cases, car bumpers, interior materials, shoe soles, washing machines, etc.

Conventional olefin polymers and copolymers, such as polyethylene, polypropylene, and ethylene-alphaolefin copolymers, were prepared by a heterogeneous catalyst consisting of titanium and alkylaluminum compounds. Recently, a metallocene catalyst, which is a homogeneous catalyst with an extremely high catalytic activity, has been developed and a method for preparing a polyolefin using a metallocene catalyst is studied.

Although a metallocene catalyst was already reported in the 1950s, active researches thereof were not conducted at the time it was reported due to its low activity. The research of a metallocene catalyst was accelerated after Professor Kaminsky of Germany first reported in 1976 that it exhibits a high activity using methylaluminoxane as a co-catalyst. An early single active site homogeneous catalyst was in the form of a metallocene compound of a Group 4 metal coordinated by two cyclopentadienyl ligands which are activated by methylaluminoxane (MAO). Thereafter, it was expanded to a catalytic form of "half-metallocene" which is represented by a constrained geometry catalyst (CGC) of the Dow Chemical Company, and the catalyst with such form exhibited remarkable properties in copolymerization compared to the early metallocene catalyst. In addition, since the 2000s, it is expanding to the catalytic form of "post-metallocene" which does not comprise cyclopentadienyl ligands. Most of single active site homogeneous catalysts have a common structure of '$LMX_2$'. Herein, M is the central metal; L is a spectator ligand which is always coordinated to a metal; and X is an acting ligand composed of a halogen atom, an alkyl group, etc., in which one of the two Xs is desorbed as an anion by a co-catalyst so that the central metal becomes cationic, while a polymer chain grows from the other X.

In the early 2000s, Dow Chemical Company and Symyx Technologies Inc. jointly utilized a high-throughput-screening (HTS) technology, thereby presenting a catalyst of a novel type (Journal of the American Chemical Society, 2003, 125: 4306). Since the catalyst has an '$LMX_3$' structure, it is distinguished from a conventionally known '$LMX_2$'-structured catalyst. The catalyst discovered by Dow and Symyx companies is characterized in that a spectator ligand L therein is in the form of an ether-amido chelate. Thereafter, an '$LMX_3$'-structured catalyst, in which the spectator ligand L is diversified to imine-amido, imine-enamido, aminotroponiminate, etc., was additionally developed.

However, very few of catalysts among the above developed catalysts are commercially applied to the field. Therefore, the development of a catalyst with improved polymerization ability is still required which shows a high activity even at a high temperature of at least 100° C. and has thermal stability, and is capable of preparing various grades of polyolefins by varying the central metal and the structure of a ligand.

SUMMARY

The present inventors have conducted extensive researches to discover a Group 4 transition metal compound showing an excellent catalytic activity capable of preparing a polyolefin of various grades. As a result, a Group 4 transition metal compound with a novel structure in which a ligand in a chelate form similar to phenanthroline is coordinated has thermal stability as well as an excellent catalytic activity, and thus can be used in a polyolefin polymerization reaction at a high temperature. In addition, the present invention was completed by confirming that it is possible to synthesize a polyolefin in which the grade is adjusted according to the type of a central metal and a ligand.

An object of the present invention is to provide a novel Group 4 transition metal compound.

Another object of the present invention is to provide a method for preparing the Group 4 transition metal compound.

Yet another object of the present invention is to provide a catalyst composition comprising the Group 4 transition metal compound.

A further object of the present invention is to provide a method for preparing a polyolefin comprising a step of carrying out polymerization of an olefin monomer in the presence of the catalyst comprising the Group 4 transition metal compound.

Since the Group 4 transition metal compound of the present invention not only exhibits an excellent catalytic activity but also has remarkable thermal stability in a polyolefin synthetic reaction, it can be used in a polyolefin synthetic reaction at a high temperature. In addition, the use of the Group 4 transition metal compound as a catalyst enables adjustment of the weight average molecular weight of a synthesized polyolefin and the octane content among the polymers, by varying the types of a central metal and a ligand, and thus can be efficiently used for a polyolefin synthesis process in which the grade is adjusted.

BRIEF DESCRIPTION OF THE DRAWINGS

FIG. 1 shows a diagram illustrating an X-ray diffraction crystal structure of a Group 4 transition metal compound according to one exemplary embodiment of the present invention in which hafnium is contained therein as a central metal and 2,9-diisopropyl-1,2,3,4-tetrahydro-1,10-phenanthroline is coordinated thereto.

DETAILED DESCRIPTION

As one aspect to achieve the above objects, the present invention provides a Group 4 transition metal compound represented by the following Formula 1:

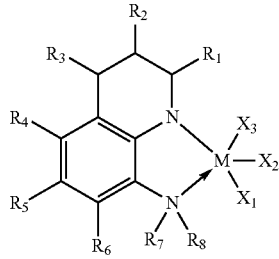

[Formula 1]

wherein,

M is a Group 4 transition metal of Ti, Zr, Hf, or Rf;

$X_1$ to $X_3$ are each independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene, or $X_1$ and $X_2$ are linked to each other and coordinated to a metal M in the form of;

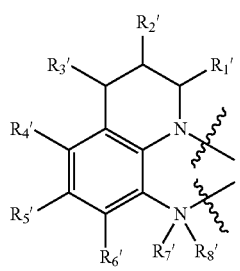

and $R_1$ to $R_8$ and $R_1'$ to $R_8'$ are each independently hydrogen, or substituted or unsubstituted $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, or $C_{1-20}$ silyl, or $R_1$ and $R_2$, $R_2$ and $R_3$, $R_4$ and $R_5$, or $R_6$ and $R_7$ are linked together to form a substituted or unsubstituted $C_{5-14}$ ring, or $R_7$ and $R_8$ together form a double bond with a nitrogen atom, to which $R_7$ and $R_8$ are bonded, wherein the double bond is linked to $R_6$ to form a substituted or unsubstituted $C_{5-14}$ conjugated ring comprising a heteroatom of O or N, wherein the substituent is each independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

As used herein, the term "substitution" may refer to a replacement of a hydrogen atom with other atoms or functional groups such as an atomic group, etc., unless otherwise stated.

In the present invention, alkyl, alkenyl, and alkynyl may be in a linear, branched, or cyclic form.

The present invention is characterized in that it provides a Group 4 transition metal compound with a novel structure in which a ligand in a chelate form similar to phenanthroline is coordinated. As stated above, a conventional single active site homogeneous catalyst has mainly been developed as a ligand coordinator having carbon, nitrogen, and oxygen atoms as a basis, e.g., cyclopentadienyl, amido, phenoxo, amine, imine, ether, etc. Recently, a ligand coordinator based on quinoline has been reported, but the structure thereof is clearly different from that of the present invention, and a bidentate coordinator based on phenanthroline has not been reported.

Preferably, the Group 4 transition metal compound may be a Group 4 transition metal compound represented by the following Formula 2:

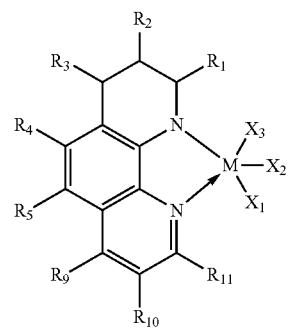

[Formula 2]

wherein, $X_1$ to $X_3$, $R_1$ and $R_5$ are the same as defined above, and $R_9$ to $R_{11}$ are each independently hydrogen, or substituted or unsubstituted $C_{1-20}$ alkyl.

$X_1$ to $X_3$ may be each independently halogen, such as chlorine, fluorine, etc., methyl, phenyl, benzyl, tolyl, or dimethylamino. More preferably, $X_1$ to $X_3$ may be all benzyl, but are not limited thereto.

Additionally, $R_1$ and $R_{11}$ may be the same or different, and may be each independently hydrogen, methyl, ethyl, isopropyl, butyl, or phenyl.

A non-limiting example of the compound may comprise the compound represented by a formula selected from the group consisting of

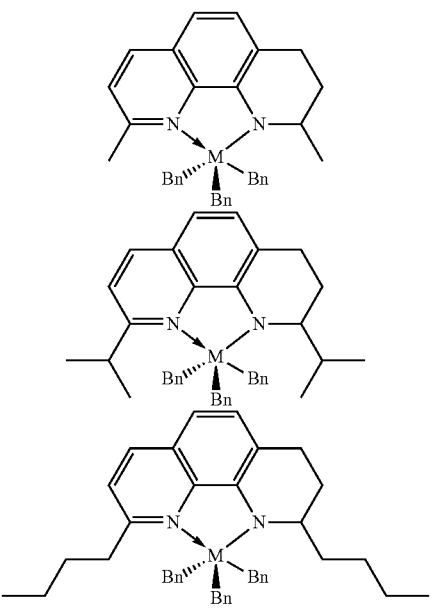

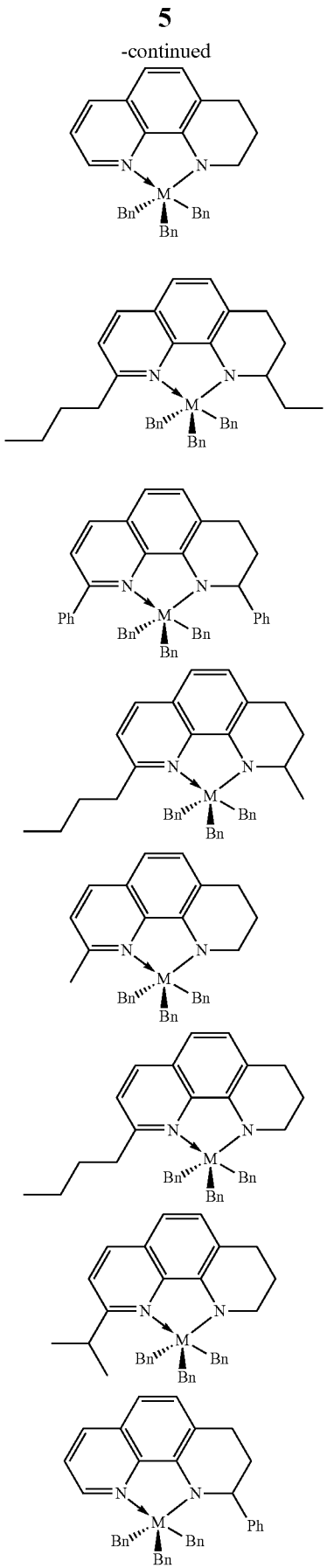
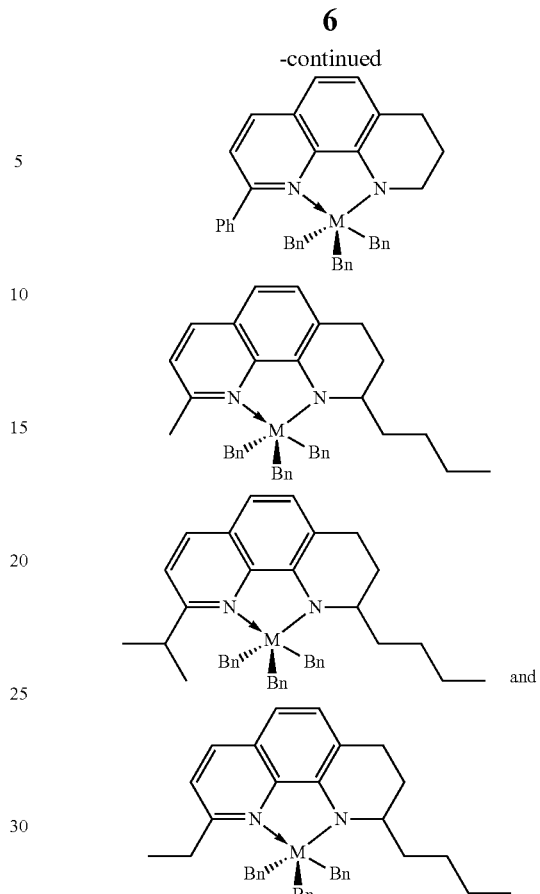

wherein M is a Group 4 transition metal of Ti, Zr, Hf, or Rf; Ph is phenyl; and Bn comprises a Group 4 transition metal compound which is benzyl.

Another aspect of the present invention provides a method for preparing a compound represented by the following Formula 1 comprising a step of reacting a compound of Formula 3 and a Group 4 transitional metal compound of Formula 4:

[Formula 1]

[Formula 3]

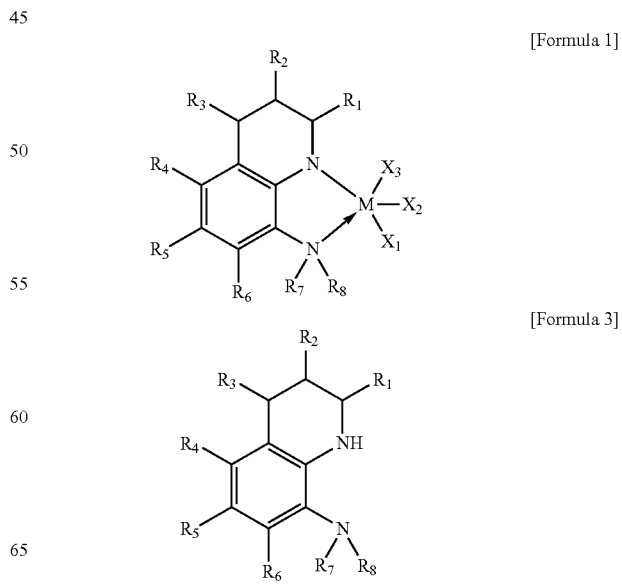

-continued

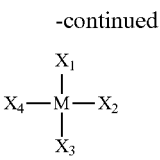

[Formula 4]

wherein,

M, $R_1$ to $R_8$, and $X_1$ to $X_3$ are the same as defined above; and $X_4$ is halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

Preferably, the compound of Formula 3 may be a phenanthroline derivative. The phenanthroline derivative may be used by purchasing a commercially available product. Alternatively, it may be used by preparing according to a synthetic method known in the art. For example, the phenanthroline derivative may be synthesized by referring to the synthetic methods published by Dr. Qing-Hua Fan (Angew. Chem. Int. Ed., 2013, 52: 7172-7176), Dr. Liang-jie Yuan (CrystEngComm, 2013, 15: 1414), Dr. Francesco Vizza (Inorganica Chimica Acta, 2008, 361: 3677), etc., but is not limited thereto. A non-limiting example of a compound of Formula 4 which can be used for preparing the Group 4 transition metal compound of the present invention may comprise 2,9-dimethyl-1,2,3,4-tetrahydro-1,10-phenanthroline, 2,9-diisopropyl-1,2,3,4-tetrahydro-1,10-phenanthroline, 2,9-dibutyl-1,2,3,4-tetrahydro-1,10-phenanthroline, 1,2,3,4-tetrahydro-1,10-phenanthroline, 9-butyl-2-ethyl-1,2,3,4-tetrahydro-1,10-phenanthroline, 2,9-diphenyl-1,2,3,4-tetrahydro-1,10-phenanthroline, 9-butyl-2-methyl-1,2,3,4-tetrahydro-1,10-phenanthroline, 9-methyl-1,2,3,4-tetrahydro-1,10-phenanthroline, 9-butyl-1,2,3,4-tetrahydro-1,10-phenanthroline, 9-isopropyl-1,2,3,4-tetrahydro-1,10-phenanthroline, 2-butyl-1,2,3,4-tetrahydro-1,10-phenanthroline, 2-isopropyl-1,2,3,4-tetrahydro-1,10-phenanthroline, 2-methyl-1,2,3,4-tetrahydro-1,10-phenanthroline, 2-phenyl-1,2,3,4-tetrahydro-1,10-phenanthroline, 9-phenyl-1,2,3,4-tetrahydro-1,10-phenanthroline, 2-butyl-9-methyl-1,2,3,4-tetrahydro-1,10-phenanthroline, 2-butyl-9-isopropyl-1,2,3,4-tetrahydro-1,10-phenanthroline, and 2-butyl-9-ethyl-1,2,3,4-tetrahydro-1,10-phenanthroline.

Preferably, in the above Formulas, $X_1$ to $X_4$ may be all benzyl.

In the above reaction, the compound of Formula 3 and the compound of Formula 4 may preferably be reacted at a molar ratio of 1:0.9 to 1:1.2, but are not limited thereto.

Additionally, the reaction may preferably be carried out in a hydrocarbon solvent selected from the group consisting of a $C_{5-10}$ aliphatic or aromatic cyclic hydrocarbon unsubstituted or substituted with halogen, a $C_{1-10}$ saturated or unsaturated hydrocarbon unsubstituted or substituted with halogen, and a mixture thereof. More preferably, the hydrocarbon solvent may be pentane, hexane, heptane, cyclohexane, methylcyclohexane, benzene, toluene, xylene, dichloromethane, chloroethane, dichloroethane, chlorobenzene, or a mixture thereof, but is not limited thereto.

In particular, the hydrocarbon solvent may be used in an amount of 100 to 1000 parts by weight based on 100 parts by weight of the total combined amount of a compound of Formula 3 and a compound of Formula 4, but is not limited thereto.

In the specific exemplary embodiment of the present invention, a phenanthroline derivative as the compound of Formula 3, and a Group 4 transition metal organic compound, e.g., tetrabenzylzirconium, tetrabenzylhafnium, or tetrabenzyltitanium, were added to a reactor along with a hydrocarbon solvent, such as toluene, etc. In addition, the reaction was allowed to proceed while stirring at a temperature from 0° C. to 100° C., e.g., at 20° C. to 30° C., for 1 hour to 30 hours. A transition metal compound with a higher yield may be obtained by carrying out the reaction under the above conditions, but is not limited thereto. Further, the above reaction conditions may appropriately be adjusted according to the combination of two reactants and a solvent.

Furthermore, the above preparation method may further comprise additional conventional post-treatment processes, e.g., removal of the solvent and unreacted compounds, washing and drying the resultant thereof, etc., after the reaction is completed. The solvent may be removed by evaporation under reduced pressure using a vacuum pump, etc., but is not limited thereto.

Another aspect of the present invention provides a catalyst composition comprising the Group 4 transition metal compound; and at least one compound selected from the group consisting of a compound of the following Formula 5, a compound of the following Formula 6, and a compound of the following Formula 7 or Formula 8:

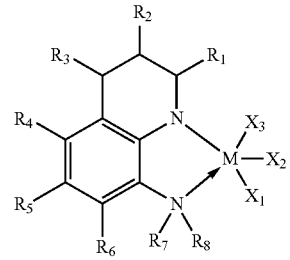

[Formula 1]

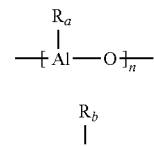

[Formula 5]

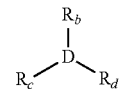

[Formula 6]

$[L\text{---}H]^+[Z(A)_4]^-$

[Formula 7]

$[L]^+[Z(A)_4]^-$

[Formula 8]

wherein,

M, $R_1$ to $R_8$, and $X_1$ to $X_3$ are the same as defined above;

$R_a$ is hydrogen, halogen, or $C_{1-20}$ alkyl, $C_{3-20}$ cycloalkyl, $C_{6-40}$ aryl or $C_{6-40}$ alkylaryl unsubstituted or substituted with halogen;

n is an integer of at least 2;

D is aluminum or boron;

$R_b$ to $R_d$ are the same or different, and are each independently hydrogen, halogen, or $C_{1-20}$ alkyl, $C_{3-20}$ cycloalkyl, $C_{1-20}$ alkoxy, $C_{6-40}$ aryl, $C_{6-40}$ alkylaryl or $C_{6-40}$ arylalkyl unsubstituted or substituted with halogen;

L is a neutral or cationic Lewis acid;

Z is a Group 13 element; and

A is substituted or unsubstituted $C_{6-20}$ aryl or substituted or unsubstituted $C_{1-20}$ alkyl.

Preferably, the catalyst composition of the present invention may comprise the compound of Formula 5, the compound of Formula 6, or a mixture thereof; and the compound of Formulas 7 or 8.

Preferably, the catalyst composition of the present invention may comprise the compound of Formula 1; the compound of Formula 5, the compound of Formula 6, or a mixture thereof; and the compound of Formula 7 or 8 at a molar ratio of 1:1 to 5:20 to 500.

The compound of Formula 5 may be aluminoxane, preferably alkylaluminoxane. A non-limiting example of the alkylaluminoxane is methylaluminoxane, ethylaluminoxane, isobutylaluminoxane, butylaluminoxane, etc., and preferably methylaluminoxane may be used, but is not limited thereto. The alkylaluminoxane may be prepared by a method known in the art, which is a method of adding an appropriate amount of water to trialkylaluminum, or reacting a water-containing hydrocarbon compound or an inorganic hydrate salt with trialkylaluminum, etc., but is not limited thereto. In addition, the alkylaluminoxane may be used by purchasing commercially available alkylaluminoxane. In a case in which alkylaluminoxane is prepared by a conventional preparation method, aluminoxane in the combined shape of linear- and cyclic-forms thereof may be obtained.

The compound of Formula 6 may preferably be an organic compound containing a Group 13 metal, e.g., aluminum or boron. In Formula 6, three substituents are the same or different. A non-limiting example of the compound of Formula 6 comprises trimethylaluminum, dimethylaluminum chloride, methoxydimethylaluminum, methylaluminum dichloride, triethylaluminum, diethylaluminum chloride, methoxydiethylaluminum, ethylaluminum dichloride, tripropylaluminum, dipropylaluminum chloride, propylaluminum dichloride, triisopropylaluminum, tributylaluminum, triisobutylaluminum, diisobutylaluminum hydride, tricyclopentylaluminum, tripentylaluminum, triisopentylaluminum, trihexylaluminum, trioctylaluminum, ethyldimethylaluminum, diethyl(methyl)aluminum, triphenylaluminum, tri-p-tolylaluminum, ethoxydimethylaluminum, trimethylboron, triethylboron, triisobutylboron, tripropylboron, tributylboron, tripentafluorophenylboron, etc.

The compound of Formula 7 or 8 may indicate methyldioctadecylammonium tetrakis(pentafluorophenyl)borate ([HNMe$(C_{18}H_{37})_2$]$^+$[B$(C_6F_5)_4$]$^-$), trimethylammonium tetrakis(phenyl)borate, triethylammonium tetrakis(phenyl)borate, tripropylammonium tetrakis(phenyl)borate, tributylammonium tetrakis(phenyl)borate, trimethylammonium tetrakis(p-tolyl)borate, tripropylammonium tetrakis(p-tolyl)borate, trimethylammonium tetrakis(o,p-dimethylphenyl)borate, triethylammonium tetrakis(o,p-dimethylphenyl)borate, trimethylammonium tetrakis(p-trifluoromethylphenyl)borate, tributylammonium tetrakis(p-trifluoromethylphenyl)borate, tributylammonium tetrakis(pentafluorophenyl)borate, diethylammonium tetrakis(pentafluorophenyl)borate, triphenylphosphonium tetrakis(phenyl)borate, trimethylphosphonium tetrakis(phenyl)borate, N,N-diethylanilinium tetrakis(phenyl)borate, N,N-dimethylanilinium tetrakis(pentafluorophenyl)borate, N,N-diethylanilinium tetrakis(pentafluorophenyl)borate, triphenylcarbonium tetrakis(p-trifluoromethylphenyl)borate, triphenylcarbonium tetrakis(pentafluorophenyl)borate, trimethylammonium tetrakis(phenyl)aluminate, triethylammonium tetrakis(phenyl)aluminate, tripropylammonium tetrakis(phenyl)aluminate, tributylammonium tetrakis(phenyl)aluminate, trimethylammonium tetrakis(p-tolyl)aluminate, tripropylammonium tetrakis(p-tolyl)aluminate, triethylammonium tetrakis(o,p-dimethylphenyl)aluminate, tributylammonium tetrakis(p-trifluoromethylphenyl)aluminate, trimethylammonium tetrakis(p-trifluoromethylphenyl)aluminate, tributylammonium tetrakis(pentafluorophenyl)aluminate, N,N-dimethylanilinium tetrakis(phenyl)aluminate, N,N-diethylanilinium tetrakis(phenyl)aluminate, N,N-diethylanilinium tetrakis(pentafluorophenyl)aluminate, diethylammonium tetrakis(pentafluorophenyl)aluminate, triphenylphosphonium tetrakis(phenyl)aluminate, trimethylphosphonium tetrakis(phenyl)aluminate, triethylammonium tetrakis(phenyl)aluminate, tributylammonium tetrakis(phenyl)aluminate, etc., but is not limited thereto. Preferably, methyldioctadecylammonium tetrakis(pentafluorophenyl)borate ([HNMe$(C_{18}H_{37})_2$]$^+$[B$(C_6F_5)_4$]$^-$), N,N-dimethylanilinium tetrakis(pentafluorophenyl)borate, triphenylcarbonium tetrakis(pentafluorophenyl)borate, etc., may be used.

The catalyst composition of the present invention can be prepared by mixing the Group 4 transition metal compound of the present invention and the co-catalyst compound described above, and bringing the same into contact. The mixing can be carried out under an atmosphere of inert gas, such as nitrogen or argon, in the absence of a solvent or in the presence of a hydrocarbon solvent. For example, the mixing can be carried out at a temperature from 0° C. to 100° C., preferably at 10° C. to 30° C. After preparing in a hydrocarbon solvent, etc., it is possible to use the catalyst composition in the form of a solution that is evenly dissolved, or in the form of a solid powder by removing a solvent. The catalyst composition in the form of a solid powder may be obtained by solidifying a precipitate after precipitating the catalyst composition in a solution state. In addition, the catalyst composition of the present invention may be used in a form in which a Group 4 transition metal compound and a co-catalyst compound are supported in a carrier, such as silica, alumina, or a mixture thereof, or in the form of an insoluble particle of a carrier, but is not limited thereto.

In the specific exemplary embodiment of the present invention, the co-catalyst compound comprises the compound of Formula 5, the compound of Formula 6, the compound of Formula 7 or 8, or two or more compounds selected therefrom. For example, methylaluminoxane, which is a compound of Formula 5, and methyldioctadecylammonium tetrakis(pentafluorophenyl)borate ([HNMe$(C_{18}H_{37})_2$]$^+$[B$(C_6F_5)_4$]$^-$), which is a compound of Formula 7, were used by mixing the same. Herein, a catalyst composition can be prepared by sequentially adding a compound of Formula 7 or 8 and a compound of Formula 5 and/or a compound of Formula 6 into a solution of a transition metal compound dissolved in a hydrocarbon solvent, and mixing the same. In order to provide a catalyst composition exhibiting a high activity in polyolefin synthesis, a transition metal compound, a compound of Formula 5, and/or a compound of Formula 6, and a compound of Formula 7 or 8 are used in the ratio described above, i.e., a molar ratio of 1:1 to 5:20 to 500.

Another aspect of present invention provides a method for preparing a polyolefin comprising a step of carrying out polymerization of an olefin monomer in the presence of the catalyst composition.

Examples of an olefin monomer capable of being used in the preparation method according to the present invention are an ethylene, an alphaolefin, a cycloolefin, etc., and dien-, triene-, and styrene-olefins are also can be used. The alphaolefin comprises an aliphatic olefin of $C_{3-12}$, e.g., that of $C_{3-8}$. Specifically, the alphaolefin comprises propylene, 1-butene, 1-pentene, 1-hexene, 1-heptene, 1-octene, 1-decene, 1-dodecene, 1-tetradecene, 1-hexadecene, 1-octadecene, 1-eicosene, 4-methyl-1-pentene, 3-methyl-1-pentene, and 3-methyl-1-butene, 4,4-dimethyl-1-pentene, 4,4-diethyl-1-hexene, 3,4-dimethyl-1-hexene, etc. The cycloolefin comprises a cyclic-olefin of $C_{3-24}$, e.g., that of $C_{4-18}$. Specifically, the cycloolefin comprises vinylcyclohexane, vinylcycloheptane, cyclopentene, cycloheptene, cyclobutene, cyclohexene, 3-methylcyclohexene, cyclooctene, tetracyclodecen, octacyclodecen, dicyclopentadiene, norbornene, 5-methyl-2-norbornene, 5-ethyl-2-norbornene, 5-isobutyl-2-norbornene, 5,6-dimethyl-2-norbornene, 5,5,6-trimethyl-2-norbornene, ethylenenorbornenetetracyclodecen, etc. The dien- and triene-olefins comprise a polyolefin of $C_{4-26}$ which includes two or three double bonds. Specifically, the dien- and triene-olefins comprise isoprene, 1,3-butadiene, 1,4-pentadiene, 1,4-hexadiene, 1,5-hexadiene, 1,9-decadien, 2-methyl-1,3-butadiene, cyclopentadiene, etc. The styrene-olefin comprises styrene or styrene substituted with C1-10 alkyl, alkoxy, or halogenated alkyl, halogen, amine, silyl, etc. Specifically, the styrene-olefin comprises styrene, p-methylstyrene, allylbenzene, divinylbenzene, etc.

In the method for preparing a polyolefin according to the present invention, the olefin monomer can be used solely or in a mixture of two or more kinds thereof. Preferably, the method may use a compound of at least one kind selected from the group consisting of ethylene, propylene, 1-butene, 1-hexene, 1-octene, and 1-decene, but is not limited thereto.

Additionally, the olefin monomer may solely be polymerized, or the olefin monomer of two or more kinds or a polymer thereof may be copolymerized to form an alternating copolymer, a random copolymer, or a block copolymer.

In the method for preparing a polyolefin according to the present invention, the amount of the catalyst composition to be used is not particularly limited. However, for example, in a reaction system to be polymerized, a central metal concentration in the Group 4 transition metal compound of the present invention can be in the range of $1 \times 10^{-5}$ mol/L to $9 \times 10^{-5}$ mol/L. Additionally, the temperature and pressure during polymerization are variable, depending on the types of reactants and reaction conditions, and thus are not particularly limited. However, polymerization can be carried out at a temperature of 0° C. to 200° C. For example, it can be carried out at a temperature of 100° C. to 180° C., and for slurry or gas-phase polymerization, it can be carried out at a temperature of 0° C. to 120° C., and preferably at a temperature of 60° C. to 100° C. Meanwhile, the polymerization pressure may be 1 bar to 150 bars, e.g., 30 bars to 90 bars, and pressure adjustment in the above range can be adjusted by injection of an olefin monomer gas used for the reaction.

For example, the polymerization reaction can be carried out in a batch type, a semi-continuous type, or a continuous type. The polymerization reaction can also be carried out with steps of two or more having different reaction conditions, and the molecular weight of a finally obtained polymer can be adjusted by a method of varying a polymerization temperature or injecting hydrogen into a reactor.

EXAMPLES

Hereinbelow, the present invention will be described in detail with accompanying exemplary embodiments. However, the exemplary embodiments disclosed herein are only for illustrative purposes and should not be construed as limiting the scope of the present invention.

Example 1: Synthesis of Group 4 Transition Metal Compound to which 2,9-dimethyl-1,2,3,4-tetrahydro-1,10-phenanthroline is Coordinated and in which Zirconium is Included as Central Metal

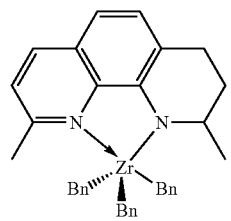

2,9-dimethyl-1,2,3,4-tetrahydro-1,10-phenanthroline (37 mg, 0.17 mmol; ligand 1) and tetrabenzylzirconium (79 mg, 0.17 mmol) were each dissolved in toluene (0.5 mL), and the ligand 1 solution was added to a tetrabenzylzirconium solution. The resultant was stirred for 30 minutes, and then the solvent was removed using a vacuum pump.

1H NMR ($C_6D_6$): δ=7.39 (d, J=8.4 Hz, 1H, 8-phenanthroline), 6.96 (t, J=7.8 Hz, 7H), 6.81-6.69 (m, 10H), 6.38 (d, J=8.4 Hz, 1H), 4.30-4.22 (m, 1H, NCH), 2.76-2.68 (m, 1H, 4-phenanthroline), 2.62 (quartet, J=11, 7.6 Hz, 6H, $ZrCH_2$), 2.46-2.38 (m, 1H, 4-phenanthroline), 2.16 (s, 3H, $CH_3$), 1.62-1.54 (m, 1H, 3-phenanthroline), 1.50-1.42 (m, 1H, 3-phenanthroline), 0.94 (d, J=6.4 Hz, 3H, $CH_3$) ppm;

$^{13}C\{^1H\}$ NMR ($C_6D_6$): δ=156.95, 146.10, 145.89, 139.91, 139.41, 130.09, 128.98, 126.82, 126.33, 122.24, 121.94, 119.22, 114.14, 75.91, 50.17, 27.68, 25.50, 23.10, 20.83 ppm.

Example 2: Synthesis of Group 4 Transition Metal Compound to which 2,9-dibutyl-1,2,3,4-tetrahydro-1,10-phenanthroline is Coordinated and in which Zirconium is Included as Central Metal

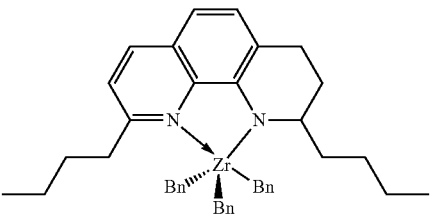

Synthesis was carried out in the same conditions and methods used in Example 1, except that 2,9-dibutyl-1,2,3,4-tetrahydro-1,10-phenanthroline (45 mg, 0.15 mmol) and the same number of moles of tetrabenzylzirconium were used (yield 91%).

$^1$H NMR ($C_6D_6$): δ=7.52 (d, J=8.4 Hz, 1H, 8-phenanthroline), 7.11-6.93 (m, 10H), 6.84 (br s, 6H), 6.78 (d, J=8.0 Hz, 1H), 6.62 (d, J=8.4 Hz, 1H), 4.28-4.20 (m, 1H, NCH), 2.80-2.60 (m, 9H), 2.47-2.36 (m, 1H, 4-phenanthroline), 1.76-1.68 (m, 1H, 3-phenanthroline), 1.64-1.57 (m, 1H, 3-phenanthroline), 1.48-1.37 (m, 2H, $CH_2$), 1.34-1.16 (m, 8H, $CH_2$), 0.96-0.81 (m, 6H, $CH_3$) ppm;

$^{13}C\{^1H\}$ NMR ($C_6D_6$): δ=161.51, 146.28, 146.13, 139.72, 139.58, 130.15, 128.97, 126.76, 126.63, 121.98, 120.76, 119.81, 114.33, 76.47, 55.03, 39.09, 33.72, 32.22, 29.23, 24.35, 23.61, 23.39, 23.11, 22.99, 14.85, 14.43 ppm.

Example 3: Synthesis of Group 4 Transition Metal Compound to which 2,9-dimethyl-1,2,3,4-tetrahydro-1,10-phenanthroline is Coordinated and in which Hafnium is Included as Central Metal

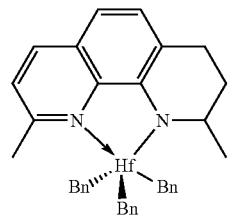

Synthesis was carried out in the same conditions and methods used in Example 1, except that tetrabenzylhafnium (82 mg, 0.15 mmol) and the same number of moles of 2,9-dimethyl-1,2,3,4-tetrahydro-1,10-phenanthroline were used.

$^1$H NMR (C$_6$D$_6$): δ=7.36 (d, J=8.0 Hz, 1H, 8-phenanthroline), 7.06-6.89 (m, 7H), 6.80 (br s, 5H), 6.76-6.67 (m, 4H), 6.65 (d, J=8.0 Hz, 1H), 6.32 (d, J=8.4 Hz, 1H), 4.48-4.39 (m, 1H, NCH), 2.77-2.65 (m, 1H, 4-phenanthroline), 2.46 (quartet, J=12, 6.8 Hz, 6H, HfCH$_2$), 2.40-2.31 (m, 1H, 4-phenanthroline), 2.12 (s, 3H, CH$_3$), 1.55-1.43 (m, 2H, 3-phenanthroline), 0.91 (d, J=6.8 Hz, 3H, CH$_3$) ppm;

$^{13}$C{$^1$H} NMR (C$_6$D$_6$): δ=157.28, 145.91, 139.85 (d, J=5.3 Hz), 130.23, 129.33, 128.56, 127.17, 126.23, 122.33, 121.88, 120.29, 114.01 ppm.

Example 4: Synthesis of Group 4 Transition Metal Compound to which 2,9-diisopropyl-1,2,3,4-tetrahydro-1,10-phenanthroline is Coordinated and in which Hafnium is Included as Central Metal

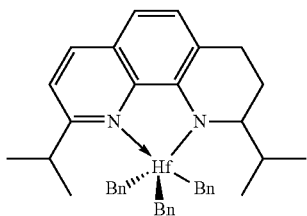

Synthesis was carried out in the same conditions and methods used in Example 1, except that 2,9-diisopropyl-1,2,3,4-tetrahydro-1,10-phenanthroline (37 mg, 0.14 mmol) and the same number of moles of tetrabenzylhafnium were used (yield 92%).

$^1$H NMR (C$_6$D$_6$): δ=7.53 (d, J=8.4 Hz, 1H, 8-phenanthroline), 7.20-6.86 (m, 12H), 6.77 (br s, 4H), 6.73 (d, J=8.8 Hz, 1H), 6.70 (d, J=8.4 Hz, 1H), 4.05-3.96 (m, 1H, NCH), 3.35-3.22 (m, 1H, Me$_2$CH), 2.75-2.57 (m, 4H, HfCH$_2$, 4-phenanthroline), 2.47 (br s, 3H, HfCH$_2$), 2.40-2.31 (m, 1H, 4-phenanthroline), 1.96-1.88 (m, 1H, 3-phenanthroline), 1.65-1.45 (m, 2H, 3-phenanthroline, Me$_2$CH), 1.11 (d, J=6.8 Hz, 3H, CH$_3$), 1.00 (d, J=6.0 Hz, 3H, CH$_3$), 0.962 (d, J=6.8 Hz, 3H, CH$_3$), 0.76 (d, J=6.8 Hz, 3H, CH$_3$) ppm;

$^{13}$C{$^1$H} NMR (C$_6$D$_6$): δ=167.66, 145.96, 140.67, 138.94, 129.96, 129.33, 128.56, 127.19, 126.84, 125.70, 122.05, 118.09, 114.48 ppm.

Example 5: Synthesis of Group 4 Transition Metal Compound to which 2,9-dibutyl-1,2,3,4-tetrahydro-1,10-phenanthroline is Coordinated and in which Hafnium is Included as Central Metal

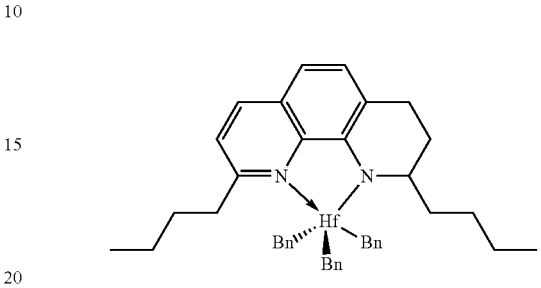

Synthesis was carried out in the same conditions and methods used in Example 1, except that 2,9-dibutyl-1,2,3,4-tetrahydro-1,10-phenanthroline (40 mg, 0.13 mmol) and the same number of moles of tetrabenzylhafnium were used (yield 90%).

$^1$H NMR (C$_6$D$_6$): δ=7.52 (d, J=8.4 Hz, 1H, 8-phenanthroline), 7.20-6.84 (m, 10H), 6.84-6.66 (m, 6H), 6.72 (d, J=8.0 Hz, 1H), 6.62 (d, J=8.4 Hz, 1H), 4.38-4.29 (m, 1H, NCH), 2.84-2.62 (m, 3H, 4-phenanthroline, CH$_2$), 2.61-2.42 (m, 6H, HfCH$_2$), 2.42-2.32 (m, 1H, 4-phenanthroline), 1.83-1.75 (m, 1H, 3-phenanthroline), 1.57-1.46 (m, 1H, 3-phenanthroline), 1.46-1.36 (m, 2H, CH$_2$), 1.34-1.13 (m, 9H, CH$_2$), 0.95-0.78 (m, 6H, C$_{H3}$) ppm;

$^{13}$C{$^1$H} NMR (C$_6$D$_6$): δ=161.83, 146.25, 140.10, 139.54, 130.31, 127.22 126.60, 122.02, 120.83, 114.07, 53.92, 38.55, 33.80, 32.14, 29.16, 24.21, 23.63, 23.36, 22.99, 22.78, 14.86, 14.43 ppm.

Examples 6 to 10: Synthesis of Ethylene and 1-Octene Copolymers

In a dry box, a solution (1.0 M, 1-octene 4.0 g, 30 mL), in which 1-octene is dissolved in methylcyclohexane as a co-monomer, and a methyl aluminoxane solution (scavenger, 7% Al toluene solution, 29 mg, 75 mmol Al) which, as a co-catalyst, was used to remove water and oxygen were added into a high-pressure polymerization reactor. In addition, the temperature of the high-pressure polymerization reactor was raised to 100° C. outside the dry box. The transition metal compounds (1.0 mmol) prepared in each of Examples 1 to 5 were dissolved in toluene, and then methyl dioctadecyl ammonium tetrakis(pentafluorophenyl)borate ([HNMe(C$_{18}$H$_{37}$)$_2$]$^+$[B(C$_6$F$_5$)$_4$]$^-$, 1.2 mmol) and a methyl aluminoxane solution (7% Al toluene solution, 19 mg, 50 mmol Al, Al/Hf or Zr=125) were added therein in a sequential order. Toluene was further added in the reaction mixture to make the total solution to be 3 mL, thereby preparing an activated catalyst composition. The catalyst composition was injected into the high-pressure polymerization reactor using a syringe, and ethylene was injected at a pressure of 435 psig in the temperature range shown in Table 1 below. In addition, ethylene and 1-octene were then polymerized for 3 minutes. Ethylene gas was vented, and methanol (10 mL) was added at 0° C. to complete the reaction. The formed white sold compound was filtered and then dried in a vacuum oven at 150° C. for several hours to prepare polyolefins, e.g., ethylene and 1-octene copolymers. The results of each experiment are shown in Table 1.

TABLE 1

| Example | Catalyst | Yield (g) | Activity | [1-octene] | Mw | Mw/Mn | Tm (° C.) |
|---|---|---|---|---|---|---|---|
| 6 | Example 4 | 0.77 | 15.4 | 2.9 | 141272 | 4.18 | 118.2 |
| 7 | Example 3 | 0.52 | 10.4 | 1.5 | 134086 | 3.26 | 118.8 |
| 8 | Example 1 | 1.20 | 24.0 | 4.3 | 383528 | 15.8 | 115.3 |
| 9 | Example 5 | 0.44 | 8.8 | 1.8 | 93256 | 3.6 | 119.7 |
| 10 | Example 2 | 1.38 | 28.0 | 4.2 | 197053 | 8.4 | 120.3 |

Property Evaluation (1) Active unit: Kg (polyolefin)/mmol (catalytic center metal)·hr (2) 1-octene content (unit: mol %): 1-octene content in the polyolefin obtained by analysis of $^1$H NMR spectroscopy (3) Weight average molecular weight (Mw, unit: g/mol): measurements were made using a gel permeation chromatography (GPC) based on polystyrene.

(4) Melting temperature (Tm, unit: ° C.): measurements were made using a Differential Scanning Calorimeter 2920 (DSC) manufactured by TA company. Specifically, a temperature was raised to 200° C., maintained for 5 minutes, lowered to 30° C., and raised again to obtain the a DSC curve, thereby determining its maximum peak value as a melting temperature. In particular, the raising and lowing rate of the temperature was 10° C./min, and the melting temperature was determined during the second rise of the temperature.

As shown in Table 1 above, it was confirmed that when a polyolefin was prepared using the catalyst composition comprising the Group 4 transition metal compound of the present invention, it exhibited a high activity even at a high temperature of 100° C. or more. In particular, the polyolefin obtained from Examples 8 and 10, which were synthesized using a catalyst composition comprising the transition metal compound obtained from Examples 1 and 2, exhibited a relatively high weight average molecular weight, and the content of 1-octene was also high. From the above result, it was confirmed that the molecular weight of the produced polyolefin is adjustable according to the type of a central metal and the structure of a ligand coordinated to a transition metal compound contained in the catalyst composition used (range of weight average molecular weight is 90,000 to 380,000). In addition, it was also confirmed that the content of 1-octene was also varied in the range of a certain level (1.5 to 4.3 mol %)

Although the preferred embodiment(s) of the present invention have(has) been disclosed for illustrative purposes, those skilled in the art will appreciate that various modifications, additions, and substitutions are possible, without departing from the scope of spirit of the invention as disclosed in the accompanying claims.

The invention claimed is:

1. A Group 4 transition metal compound represented by the following Formula 1:

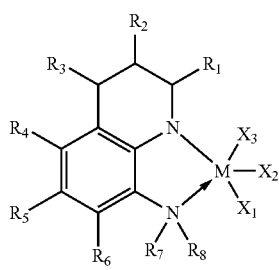

Formula 1 wherein,

M is a Group 4 transition metal of Ti, Zr, or Hf;

$X_1$ to $X_3$ are each independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ dialkylamido, $C_{6-20}$ diarylamido, or $C_{1-20}$ alkylidene, or $X_1$ and $X_2$ are linked to each other and coordinated to a metal M in the form of

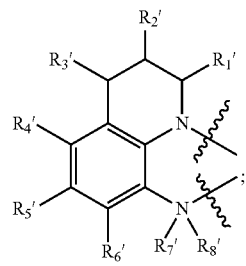

and $R_1$ to $R_8$ and $R_1'$ to $R_8'$ are each independently hydrogen, or substituted or unsubstituted $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, or $C_{1-20}$ silyl, and $R_1$ and $R_2$, $R_2$ and $R_3$, $R_4$ and $R_5$, or $R_6$ and $R_7$ are optionally linked together to form a substituted or unsubstituted $C_{5-14}$ ring, and $R_7$ and $R_8$ together form a double bond with the nitrogen atom, to which $R_7$ and $R_8$ are bonded, wherein the double bond is linked to $R_6$ to form a substituted or unsubstituted $C_{5-14}$ conjugated ring comprising the nitrogen atom as a heteroatom, and optionally comprising an additional heteroatom of O or N, wherein the substituent is each independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ dialkylamindo, $C_{6-20}$ diarylamido, or $C_{1-20}$ alkylidene.

2. The Group 4 transition metal compound of claim 1, wherein the compound is represented by the following Formula 2:

Formula 2

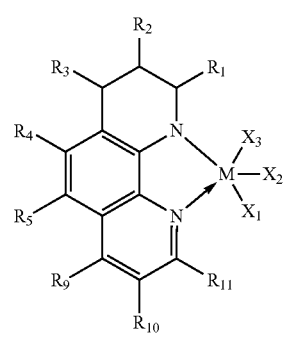

wherein,

R$_9$ to R$_{11}$ are each independently hydrogen, or substituted or unsubstituted C$_{1-20}$ alkyl.

3. The Group 4 transition metal compound of claim 2, wherein X$_1$ to X$_3$ are all benzyl.

4. The Group 4 transition metal compound of claim 2, wherein R$_1$ and R$_{11}$ are the same or different, and are each independently selected from the group consisting of hydrogen, methyl, ethyl, isopropyl, butyl, and phenyl.

5. The Group 4 transition metal compound of claim 4, wherein the compound is represented by a formula selected from the group consisting of

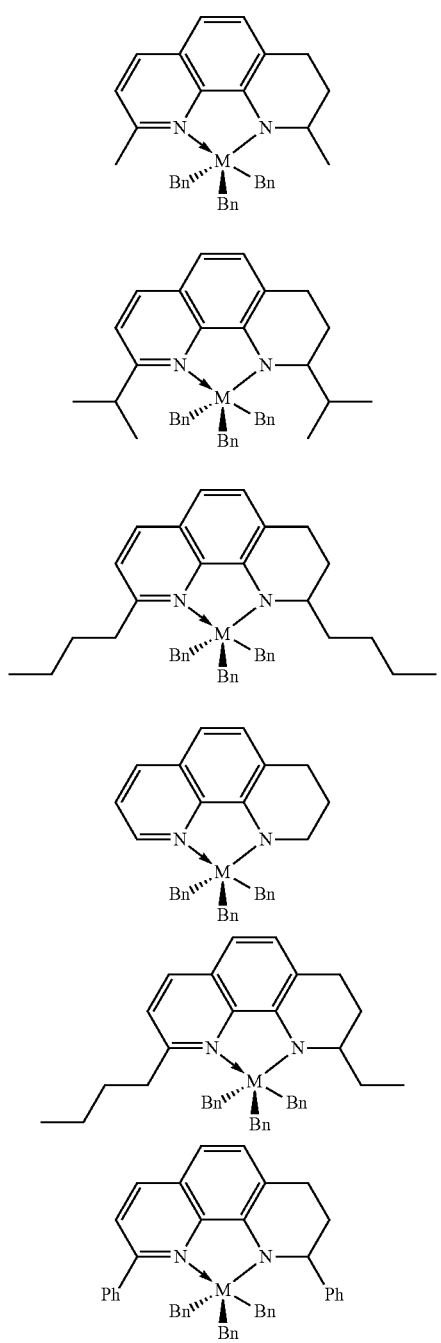

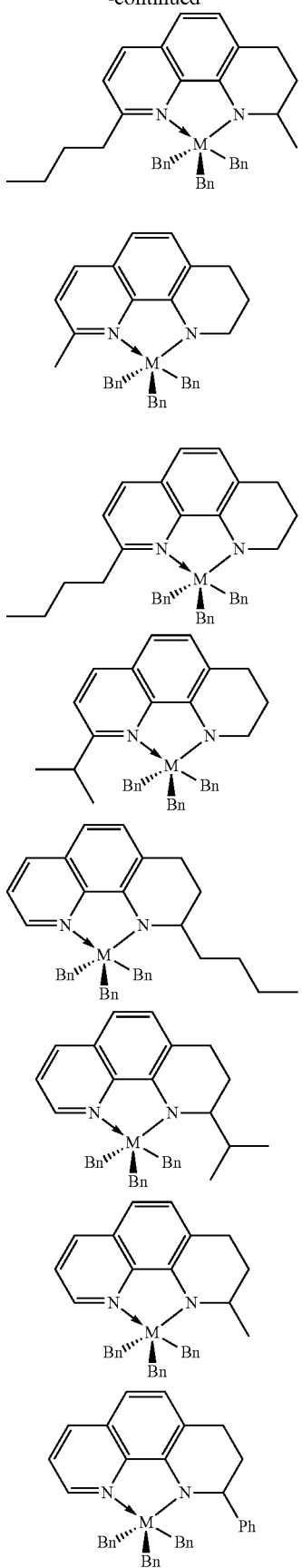

-continued

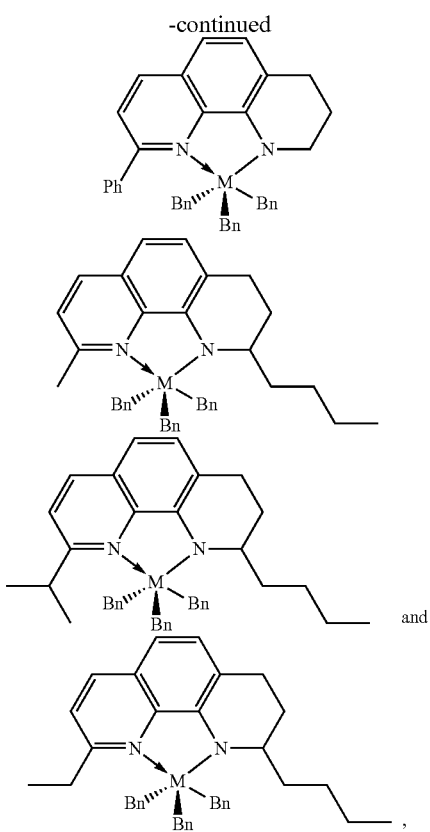

where in M is a group transition metal of Ti, Zr, or Hf; Ph is phenyl; and Bn is benzyl.

6. A method for preparing the compound of claim 1, comprising a step of reacting a compound of Formula 3 and a Group 4 transition metal compound of Formula 4:

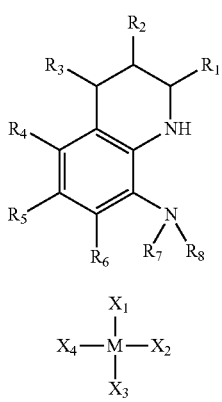

wherein,
and
$X_4$ is halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

7. The method of claim 6, wherein the compound of Formula 3 is a phenanthroline derivative.

8. The method of claim 6, wherein $X_1$ to $X_4$ are all benzyl.

9. The method of claim 6, wherein the compound of Formula 3 and the compound of Formula 4 are reacted at a mole ratio of 1:0.9 to 1:1.2.

10. The method of claim 6, wherein the reaction is carried out in a hydrocarbon solvent selected from the group consisting of a $C_{5-10}$ aliphatic or aromatic cyclic hydrocarbon unsubstituted or substituted with halogen, a $C_{1-10}$ saturated or unsaturated acyclic hydrocarbon unsubstituted or substituted with halogen, and a mixture thereof.

11. The method of claim 10, wherein the hydrocarbon solvent is pentane, hexane, heptane, cyclohexane, methylcyclohexane, benzene, toluene, xylene, dichloromethane, chloroethane, dichloroethane, chlorobenzene, or a mixture thereof.

12. The method of claim 10, wherein the hydrocarbon solvent is present in an amount of 100 to 1000 parts by weight based on 100 parts by weight of the total combined amount of the compound of Formula 3 and the compound of Formula 4.

13. A catalyst composition comprising the Group 4 transition metal compound of claim 1; and at least one compound selected from the group consisting of a compound of Formula 5, a compound of Formula 6, a compound of Formula 7, and a compound of Formula 8:

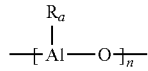

Formula 5

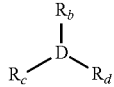

Formula 6

$[L'\text{---}H]^+[Z(A)_4]^-$

Formula 7

$[L]^+[Z(A)_4]^-$

Formula 8 wherein,
$R_a$ is hydrogen, halogen, e $C_{1-20}$ alkyl, $C_{3-20}$ cycloalkyl, $C_{6-40}$ aryl or $C_{6-40}$ alkylaryl unsubstituted or substituted with halogen;
n is an integer of at least 2;
D is aluminum or boron;
$R_b$ to $R_d$ are the same or different, and are each independently hydrogen, halogen, $C_{1-20}$ alkyl, $C_{3-20}$ cycloalkyl, $C_{1-20}$ alkoxy, $C_{6-40}$ aryl, $C_{6-40}$ alkylaryl or $C_{6-40}$ arylalkyl unsubstituted or substituted with halogen;
L is a neutral or cationic Lewis acid;
L' is a Lewis base;
Z is a Group 13 element; and
A is substituted or unsubstituted $C_{6-20}$ aryl or substituted or unsubstituted $C_{1-20}$ alkyl.

14. The catalyst composition of claim 13, wherein the composition comprises the compound of Formula 5, the compound of Formula 6 or a mixture thereof; and the compound of Formula 7 or 8.

15. The catalyst composition of claim 14, comprising the compound of Formula 1; the compound of Formula 5, the compound of Formula 6, or a mixture thereof; and the compound of Formula 7 or 8 at a molar ratio of 1:1 to 5:20 to 500.

16. A method for preparing a polyolefin, comprising a step of carrying out polymerization of an olefin monomer in the presence of the catalyst composition of claim 13.

17. The method for preparing the polyolefin of claim 16, wherein the olefin monomer is at least one compound selected from the group consisting of ethylene, propylene, 1-butene, 1-hexene, 1-octene, and 1-decene.

* * * * *